United States Patent [19]

Nottage et al.

[11] Patent Number: 5,895,351

[45] Date of Patent: Apr. 20, 1999

[54] TISSUE DISTRACTING CANNULA

[75] Inventors: Wesley Nottage, Laguna Hills, Calif.; James A. Boucher, Warsaw, Ind.

[73] Assignee: Arthrotek Inc., Warsaw, Ind.

[21] Appl. No.: 09/020,124

[22] Filed: Feb. 6, 1998

[51] Int. Cl.[6] ............................................. A61M 5/32
[52] U.S. Cl. ...................................... 600/201; 604/175
[58] Field of Search .................................. 604/174, 175; 600/201

[56] References Cited

U.S. PATENT DOCUMENTS

| | | | |
|---|---|---|---|
| 52,014 | 1/1866 | Bartlett . | |
| 58,709 | 10/1866 | Worral . | |
| 400,589 | 4/1889 | Molesworth . | |
| 2,804,796 | 9/1957 | Devine | 85/1 |
| 2,850,788 | 9/1958 | Rypysc | 27/21 |
| 3,132,645 | 5/1964 | Gasper . | |
| 3,352,301 | 11/1967 | Abelson . | |
| 4,350,147 | 9/1982 | Sarrine . | |
| 4,608,965 | 9/1986 | Anspach, Jr. et al. . | |
| 5,165,387 | 11/1992 | Woodson . | |
| 5,226,890 | 7/1993 | Ianniruberto et al. . | |
| 5,290,249 | 3/1994 | Foster et al. | 604/174 |
| 5,354,302 | 10/1994 | Ko | 606/104 |
| 5,364,367 | 11/1994 | Banks et al. | 604/174 |
| 5,370,625 | 12/1994 | Shichman | 604/174 |
| 5,372,583 | 12/1994 | Roberts et al. | 604/175 |
| 5,449,257 | 9/1995 | Giannuzzi | 411/31 |
| 5,460,170 | 10/1995 | Hammerslag | 128/20 |
| 5,484,420 | 1/1996 | Russo | 604/178 |
| 5,556,385 | 9/1996 | Anderson | 604/174 |
| 5,573,496 | 11/1996 | McPherson et al. | 600/217 |
| 5,577,993 | 11/1996 | Zhu et al. | 600/204 |
| 5,634,882 | 6/1997 | Gagner | 600/201 |
| 5,649,949 | 7/1997 | Wallace et al. | 606/191 |
| 5,651,773 | 7/1997 | Perry et al. | 604/19 |
| 5,713,869 | 2/1998 | Morejon | 604/175 |
| 5,716,325 | 2/1998 | Bonutti | 600/204 |
| 5,716,326 | 2/1998 | Dannan | 606/204 |
| 5,728,103 | 3/1998 | Picha et al. | 606/108 |
| 5,746,720 | 5/1998 | Stouder, Jr. | 604/175 |
| 5,766,220 | 6/1998 | Moennining | 604/179 |

OTHER PUBLICATIONS

Advertising Flyer of a Cannula by Arthrex Naples FL 1997, Stephen Burkhart MD San Antonio TX.

*Primary Examiner*—Paul J. Hirsch
*Attorney, Agent, or Firm*—Ernest E. Helms

[57] ABSTRACT

A distracting cannula is provided which includes a first penetrating member having a first end and a second end. The first penetrating member has an internal surface providing a through bore operative to receive an elongated surgical instrument. The first penetrating member has an external gripping surface disposed between the first and second ends that is provided by a helical thread. A generally conical shroud has an open end for contacting the patient's skin. An opposite end of the shroud is attached to the first penetrating member near the second end. The first penetrating member first end is inserted into a portal incision of the patient's body until the shroud open end contacts the patient's skin. Torquing the tissue distracting cannula further caused the tissue gripping surface of the first penetrating member to pull the surrounding tissue upward into a cavity created by the shroud.

31 Claims, 3 Drawing Sheets

TISSUE DISTRACTING CANNULA

BACKGROUND OF THE INVENTION

The present invention relates to cannulas used to maintain an opening for elongated surgical instruments during an arthroscopic surgical procedure. More particularly the present invention relates to cannulas especially useful in orthopedic arthroscopic procedures. The present invention also relates to methods to use such aforementioned cannulas.

Athletes often place large and or repetitive stresses upon their joints and surrounding tissues. When a serious injury occurs it can often require the use of orthopedic surgery.

In the past orthopedic surgery typically required a rather large incision in the skin and underlying tissue that surrounded the injury. The amount of tissue trauma was a large factor in determining the recovery time for certain surgical operations. The amount of tissue trauma is also a large factor in determining how much pain the patient feels perioperatively.

It is highly desirable that an injured athlete be able to return to his or her athletic endeavor as soon as possible. Therefore surgical techniques to treat athletes have been developed which minimize tissue trauma and the recovery time required. One such surgical technique is arthroscopic surgery. In arthroscopic surgery a relatively small incision called a portal is made in the skin and underlying tissue. A cannula is inserted into the portal to maintain a passageway. Various elongated surgical tools or instruments such as an arthroscope, a stapler or a surgical clip applier are inserted within the cannula to perform a surgical procedure.

A human shoulder is formed by two main bones. The first bone is the upper arm or humerus. The second bone is the shoulder blade often referred to as the scapula. An end or head of the scapula, called the glenoid is joined with the humerus to create a glenohumeral cavity. The glenohumeral cavity provides a ball and socket joint. An articular cartilage covers the end of the humerus and an interface of the glenoid. The ball and socket joint is surrounded by fibrous cartilage referred to as the labrum. The two bones are joined by ligaments and a biceps tendon connects a biceps muscle to the shoulder. Four short muscles project from the scapula around the shoulder and fuse their tendons to form the rotator cuff. Surrounding the cuff is the subacromial bursa. The bursa provides a slippery surface for these tendons to move upon.

When surgically treating the shoulder with an arthroscopic technique, it is often required to surgically penetrate the bursa. However, during the surgery it is important to keep the bursa from collapsing. It is also important to note that many surgical procedures require additional portals into the shoulder independent from the portal of the cannula. When the cannula is inserted into the tissue of the shoulder, the tissue surrounding the cannula is displaced radially outward. The tissue underlying the cannula has a tendency to be pushed downward. Therefore in an arthroscopic surgical procedure, the cannula has a tendency to collapse work space. This collapse makes visualization difficult and complicates the procedure. It is desirable that a cannula would distract instead of collapse the surrounding tissue.

SUMMARY OF THE INVENTION

To meet the above noted desire, the present inventive tissue distracting cannula is brought forth. The present inventive tissue distracting cannula in one preferred embodiment includes a first penetrating member having a first end and a second end. The first penetrating member has an internal surface providing a through bore. The bore is operative to receive an elongated surgical instrument. The first penetrating member has an external gripping surface disposed between the first and second ends that is provided by a helical thread. A generally conical shroud receptacle member has an open end for contacting the patient's skin. An opposite end of the shroud is attached to the first penetrating member near the second end. The first penetrating member first end is torsionally inserted into a portal incision of the patient's body until the shroud open end contacts the patient's skin. Torquing the tissue distracting cannula further causes the tissue gripping surface of the first penetrating member to pull the surrounding tissue upward into a cavity created by the shroud. A working space gap is created between the tissue underlying the deltoid muscle (joint capsule or subacromial bursa) and the relatively fixed substructure of the rotator cuff and joint beneath.

Various objects and advantages of this invention will become apparent to those skilled in the art from the following detailed description of the preferred embodiment, when read in light of the accompanying drawings.

BRIEF DESCRIPTION OF THE DRAWINGS

FIG. 5 is an alternate preferred embodiment tissue distracting cannula according to the present invention wherein a position of connection of a shroud of the cannula with respect to a penetration member of the cannula is adjustable.

DETAILED DESCRIPTION OF THE PREFERRED EMBODIMENT

Figure 1:
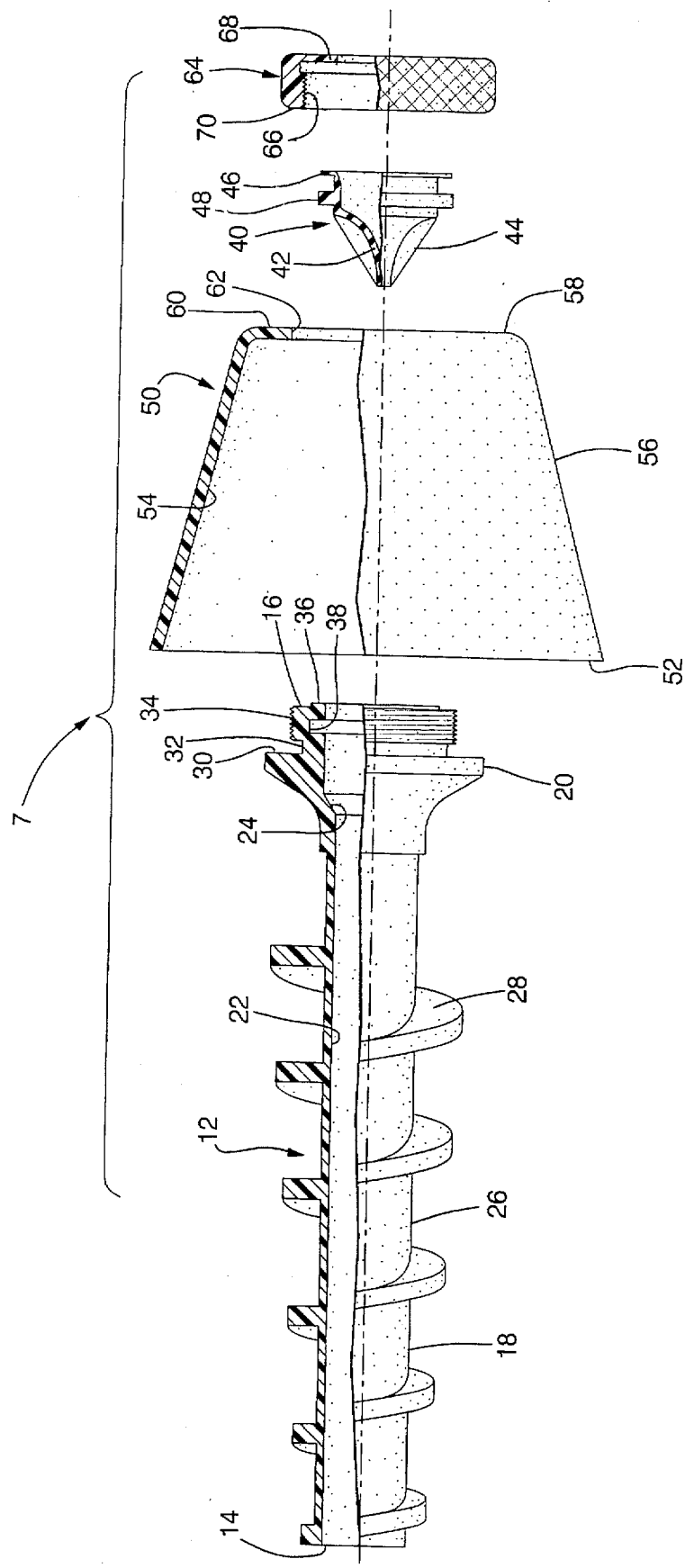
FIG. 1 is an exploded view partially sectioned of a preferred embodiment tissue distracting cannula according to the present invention.
Figure 2:
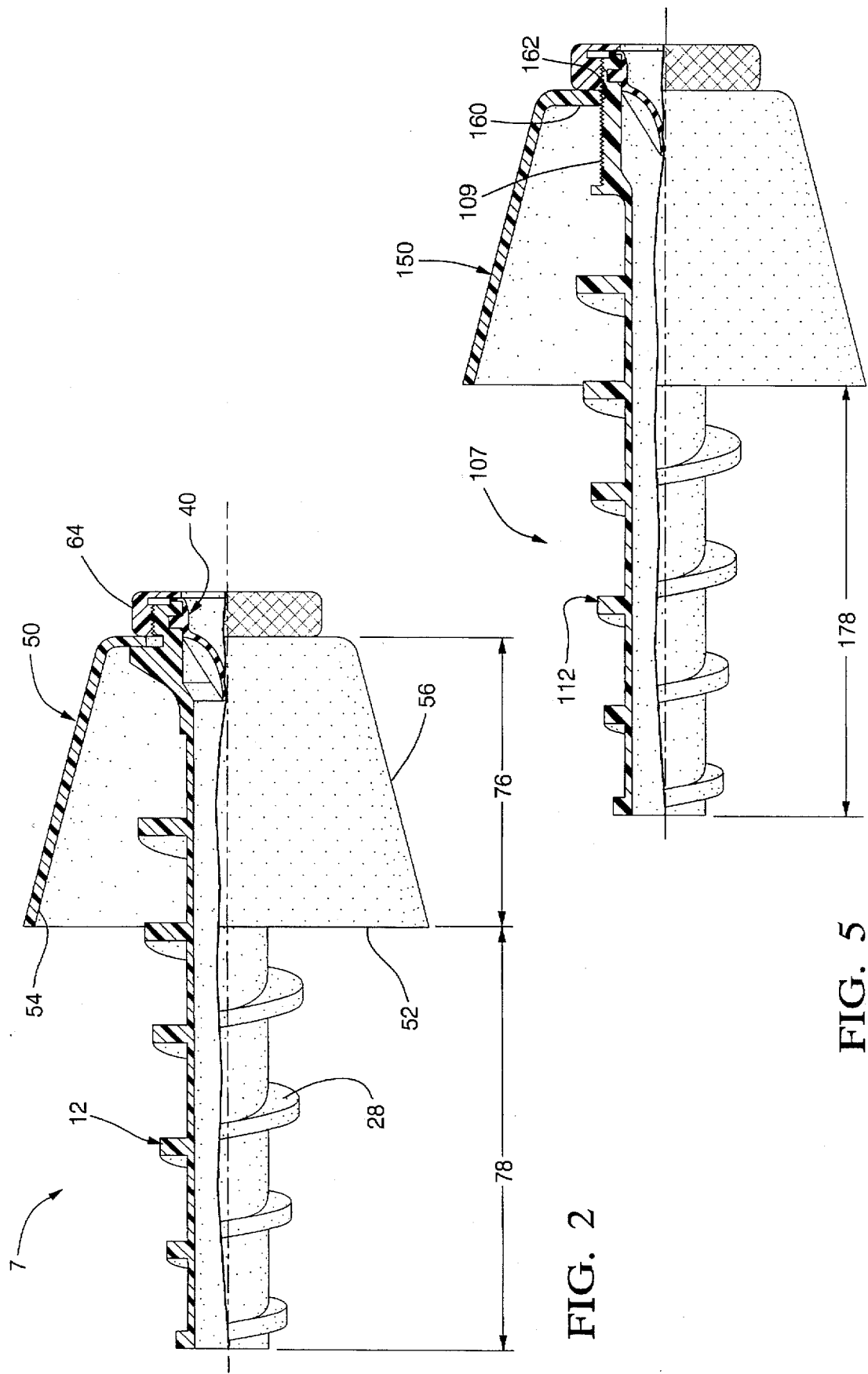
FIG. 2 is an assembled view of the tissue distracting cannula shown in FIG. 1.

Referring to FIGS. 1 and 2, the tissue distracting cannula 7 according to the present invention has a first penetrating member 12. The first penetrating member 12 can be fabricated from stainless steel or other suitable materials. In the example shown the first penetrating member 12 is fabricated from a rigid polymeric material such as acrylonitrile butadiene styrene (ABS) plastic. Ideally the first penetrating member 12 should be a clear plastic to allow visualization inside the first penetrating member of the threads and sutures used during a surgical procedure.

The first penetrating member 12 has a first end 14. The first penetrating member has a second end 16. The first penetrating member has a stem 18. The first penetrating member adjacent the second end 16 has a head 20. The head 20 is integrally formed with the stem 18. The first penetrating member stem 18 has an internal surface defining a central through bore 22. The head 20 of the first penetrating member has a multiple diameter bore 24 that is aligned with the bore 22 of the stem.

Disposed between the first and second ends 14, 16 of the first penetrating member is an external surface 26 for engaging and gripping a patient's tissue. As shown in FIG. 1, the tissue engaging or gripping surface 26 includes a helical thread 28. A thread height of the helical thread 28 descends at an acute seven degree angle in a direction toward the first penetrating member first end 14.

The head of the first penetrating member has a flange 30. Adjacent to the flange 30 is an annular indention 32. Adjacent to the annular indention 32 is a threaded outer diameter section 34. Adjacent to the threaded outer diameter section 34 is an axial lip 36. The multiple diameter bore 24 of the first penetrating member head has an annular radial groove 38.

The first penetrating member stem bore 22 and first penetrating member head bore 24 accommodate an obturator 72 (FIG. 3) during insertion of the first penetrating member 12 into a patient's body. After positioning of the tissue distracting cannula 7 into the patient's body, the first penetrating member stem bore 22 and first penetrating member head bore 24 operate to receive an elongated surgical instrument (not shown). The surgical instrument is hermetically contained within the first penetrating member head 20 by a silicon rubber seal 40. The seal 40 has two opposed lips 42 which contact one another (only one shown in section). The lips 42 are reinforced to a closed position by lateral ribs 44 to seal off the first penetrating member head bore 24. The seal 40 has an end flange 46 spaced from a locating flange 48. The locating flange 48 is fitted within the radial annular groove 38 of the first penetrating member head to hold the seal 40 in position. Typically the fit of the locating flange 48 within the radial annular groove 38 is of a slight interference fit. The seal end flange 46 covers the first penetrating member axial lip 36. The seal 40 can be replaced if it is damaged during the surgical procedure.

Removably attached with the first penetrating member is an outer receptacle member or shroud 50. The shroud 50 is generally conical in shape. The shroud 50 has a first end portion 52 that is open or communicates with the first end 14 of the first penetrating member. The shroud 50 has a raised inner surface portion 54 that defines a void or cavity wherein a patient's tissue may be distracted into. The shroud 50 has an outer surface 56 that can be torsionally gripped by a surgeon. The first end 52 of the shroud is configured to operatively contact an outer or external surface of tissue of the patient (typically the patient's skin 82) to define a bounded area of the patient's tissue. The outer surface contacted by the shroud is opposite the generally fixed substructure of the patient rotator cuff 84 and joint 86.

The shroud 50 has a second end 58 that is connected with the first penetrating member head 20. The shroud second end 58 includes an annular flat 60 that is fitted against the flange 30 of the first penetrating member head. The shroud annular flat 60 has an aperture 62 that is larger than the annular indention 32 of the first penetrating member head. Therefore, as required, the shroud 50 can be positioned in a slightly off-centered position with respect to the first penetrating member 12 to properly contact the patient's external tissue. The shroud 50 is typically fabricated from a generally rigid polymeric material such as ABS plastic. It is preferable to use a clear plastic for the shroud.

To threadably attach the shroud 50 with the first penetrating member 12 there is provided a threaded fastener or cap 64. The cap 64 has an interior threaded section 66 that engages the outer threaded section 34 of the first penetrating member head. The cap 64 also has an inner annular flap 68. When the cap 64 is fully torqued, the flap 68 has a slight spring deflection to press the end flange 46 of the seal against the axial lip 36 of the first penetrating member head. An edge 70 of the cap captures the shroud annular flat 60 against the first penetrating member head flange 30.

A height or length 76 of the shroud 50 sets a length 78 of insertion or penetration of the first penetrating member 12 into the patient's tissue within the generally bounded area. Therefore in larger patients, or for certain locations further away from the patient's orthopedic injury, a shorter shroud 50 will be utilized. For smaller patients or where the desired surgical instrument insertion location is closer to the patient's orthopedic injury, a larger shroud 50 will be selected. Typical values of the shroud length 76 are 55 mm, 65 mm, and 75 mm. The typical penetration lengths are 35 mm, 25 mm, and 15 mm respectively.

Figure 3:
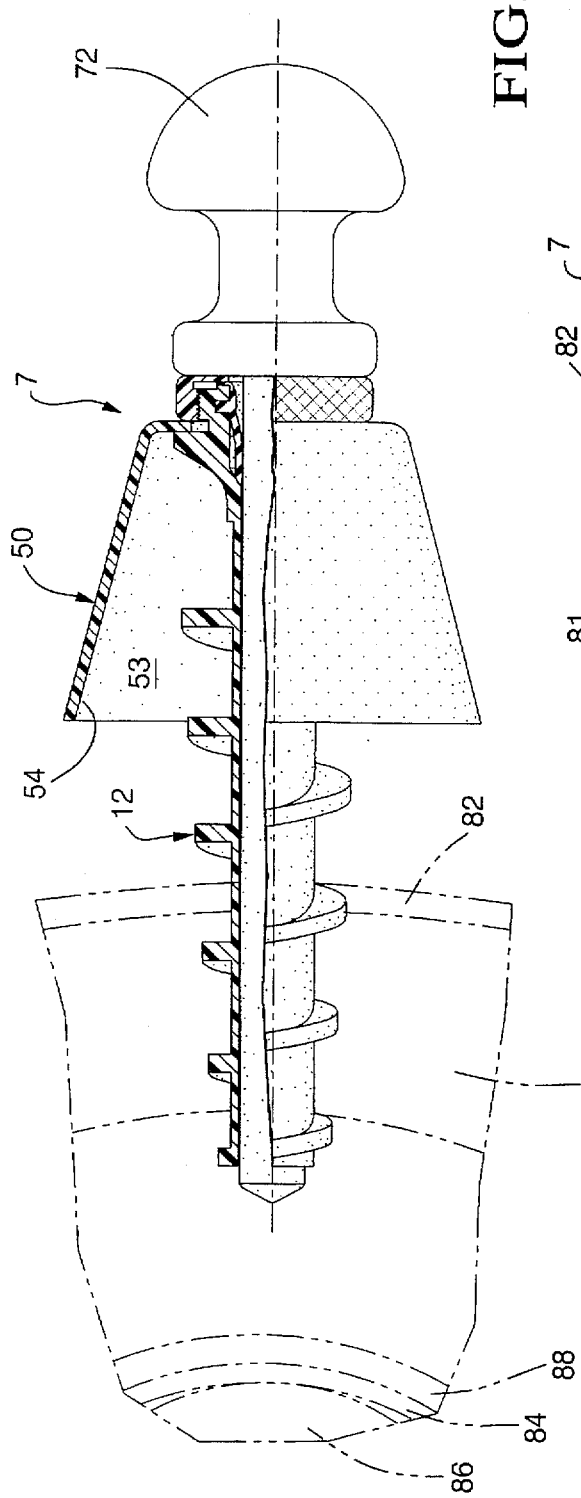
FIG. 3 is a side elevational view illustrating insertion of the tissue distracting cannula into a patient's body.
Figure 4:
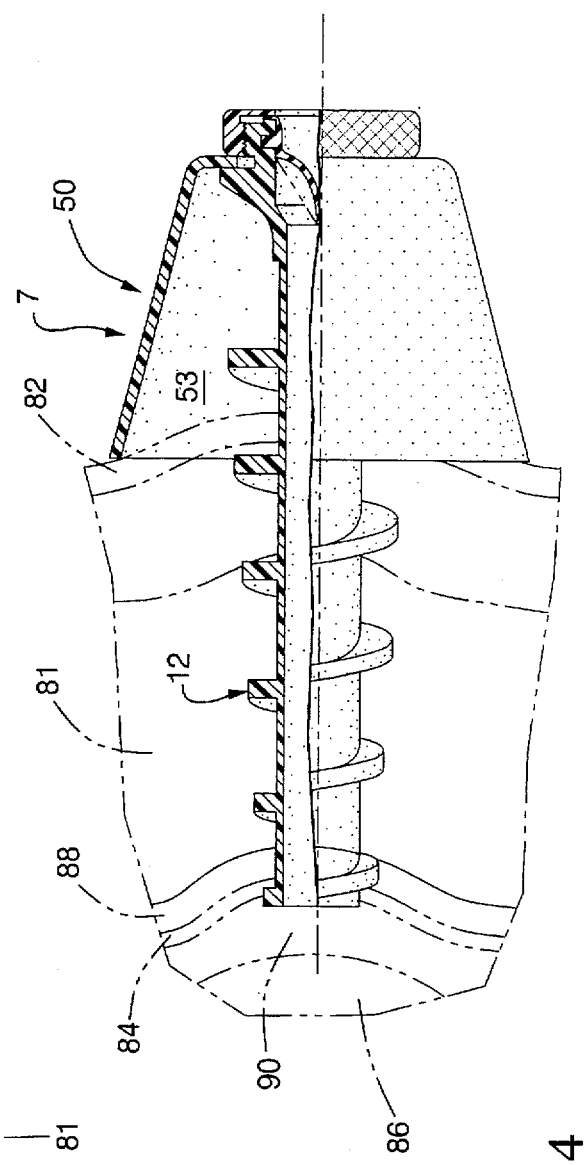
FIG. 4 is a side elevational view of a completed installation of the tissue distracting cannula.

Referring additionally to FIGS. 3 and 4, the surgeon uses a scalpel to make a 5–10 mm portal incision through the skin and underlying deltoid muscular tissue 81. The portal incision will also extend through the joint capsule and optionally through the subacromial bursa 88 depending on the desired surgical location. The surgeon will then insert the obturator 72 into the first penetrating member 12. A tip 74 of the obturator 72 will deflect the tissue radially outward so that the tissue will contact the gripping surface 26 of the first penetrating member stem 18. As the obturator 72 is pushed down, the surgeon will grab the outer surface 56 of the shroud. The surgeon torques the shroud 50 clockwise (looking toward the first penetrating member first end 14). The tissue distracting cannula 7 will be pushed downward until the shroud first end 52 embeds itself into the patient's skin 82. The shroud first end 52 forms a pull point on the patient's skin 82. Further torsional movement of the tissue distracting cannula 7 will cause the helical gripping surface 26 to grab and pull and distract the tissue surrounding (and underlying) the first penetrating member 12 upwards relative to the shroud 50. The upward movement of the tissue forces it into the cavity 53 formed by the inner surface shroud 54. The seal 40 will close off the bore 24. The bursa 88 and surrounding tissue will be distracted and pulled away from the relatively fixed substructure of the patient's rotator cuff 84 and underlying joint beneath. A workspace gap 90 or cavity of approximately 1–2 cm (depending on the patient's size) within the patient's tissue will be created adjacent to the rotator cuff 84. The surgeon will have more room adjacent the rotator cuff 84 for the surgical procedure. Pumping fluid into the bursa 88 to insure that the bursa 88 does not collapse upon the rotator cuff 84 can be assured.

The shroud 50 also gives lateral support to the first penetrating member 12 preventing wobble. Leaving surgical instruments in the first penetrating member 12 will not cause the first penetrating member 12 to be displaced from the portal. If more clearance is desired during a stage of the surgical procedure, the shroud 50 and the seal 40 can be replaced by removal of the cap 64. The first penetrating member 12 does not have to be removed from the portal to allow replacement of the shroud 50 and the seal 40.

The surgeon can see inside the tissue cavity 90 by virtue of an arthroscope (not shown) placed within the cannula 7 or through an arthroscope placed in the tissue cavity through another portal. Because the shroud 50 and penetrating member are fabricated from a clear plastic, the surgeon can see inside the cannula 7 from any where in the tissue cavity 90. The operative field is effectively enlarged since the surgeon can see the surgical instruments and sutures before they enter the tissue cavity 90.

To remove the cannula 7 from the patient's body, the surgeon can simply grab the shroud 50 and rotate it in a direction opposite its rotational direction during insertion. The penetrating member 12 will be released from the patient's body.

It is apparent to those skilled in the art, that the present tissue distracting cannula 7 can be used for glenohumeral joint work (instability). The cannula 7 will help to control edematous floppy soft tissues that obscure visualization. Also it is apparent to those skilled in the art the cannula 7 will not slide in and out of the insertion portal. Therefore the cannula 7 will not have to be reinserted or replaced during the surgical operation. Excessive fluid leakage from the tissue cavity 90 caused by technical delays to replace or reinsert the cannula 7 into the insertion portal is eliminated.

Referring to FIG. 5, an alternate preferred embodiment tissue distracting cannula 107 is presented. The cannula 107 has a penetrating member 112 that is similar to the penetrating member 12 shown in FIGS. 1–4. However the penetrating member 112 has additionally a threaded section 109. The shroud 150 has an annular flat 160 that is thickened in an area adjacent to an aperture 162. A shroud aperture is threaded to engage the threaded section 109 of the penetrating member 112. To adjust the position of connection of the shroud 150 with respect the penetrating member, the surgeon torques the shroud 150 with respect to the penetrating member 112. The positional adjustment is made to change the length 178 of insertion or penetration of the penetrating member 112 into the patient's tissue. The grip of the shroud threaded aperture 162 upon the threaded section 109 should be tight enough to prevent inadvertent movement after positional adjustment of the surgeon.

In still another embodiment of the present invention (not shown) the shroud is integral to the first penetrating member.

While the preferred embodiment has been shown and described with the cannula having a turning or threading tissue gripping surface that pulls the tissue away from the desired location, it is understood that, alternately, the cannula could have a mechanical expanding grip that is pushed beneath the tissue and then expanded to thereby grip the tissue. The cannula would then be retracted axially outwardly to engage the shroud or receptacle member and thereby distract the tissue away from the area the surgeon desires to work in.

The principal and mode of operation of this invention have been explained and illustrated in its preferred embodiments. However it must be understood that this invention may be practiced otherwise than as specifically explained and illustrated without departing from its scope.

We claim:

1. A tissue-distracting cannula for use during a surgical procedure to distract tissue away from a relatively fixed substructure, the tissue having an outer surface opposite the substructure, the tissue distracting cannula comprising:
   a receptacle member having a tissue-contacting portion and a raised portion defining a void into which distracted tissue can be received, said tissue-contacting portion operable to contact the outer surface in a manner to define a generally bounded area of the tissue;
   a penetrating member connected to said receptacle member and adapted to engage the tissue within the generally bounded area, said penetrating member selectably operable to distract the tissue into said void;
   whereby a gap is created between the tissue and the substructure.

2. A cannula as described in claim 1 wherein said tissue contacting portion is a helical thread.

3. A cannula as described in claim 2 wherein said helical thread has a descending thread height.

4. A cannula as described in claim 1 wherein said receptacle member is removable from said penetrating member.

5. A cannula as described in claim 1 wherein said receptacle member is a shroud.

6. A cannula as described in claim 1 wherein said penetrating member is fabricated from a polymeric material.

7. A cannula as described in claim 1 wherein said receptacle member and said penetrating member are fabricated from a clear plastic material.

8. A cannula as described in claim 1 wherein said connection of said receptacle member with respect to said penetrating member is positionally adjustable.

9. A tissue distracting cannula, comprising:
   an outer member configured to engage an external section of tissue;
   a penetrating member attached to said outer member, said penetrating member having an internal and an external surface, said external surface having a helical thread tissue engaging surface that is capable of grasping and pulling tissue relative to said outer member that is engaging said external section of tissue.

10. A cannula as described in claim 9 wherein said outer member is a shroud.

11. A cannula as described in claim 9 wherein said outer member is removable from said penetrating member.

12. A cannula as described in claim 9 wherein said attachment of said outer member with respect to said penetrating member is positionally adjustable.

13. A tissue distracting cannula, comprising:
   a first member having a first end and a second end, said first member having an external surface defining a tissue gripping surface disposed between said first end and said second end, and said first member having an internal surface defining a through bore from said first end to said second end, said bore being operable to receive a surgical instrument;
   a shroud attached to said first member, said shroud having an inner surface and an outer surface, said shroud inner surface being in communication with said first member first end, and said shroud inner surface defining a cavity wherein a patient's tissue may be distracted into said shroud.

14. A cannula as described in claim 13 wherein said tissue gripping surface is a helical thread.

15. A cannula as described in claim 13 wherein said first member bore has a seal for containing said surgical instrument.

16. A cannula as described in claim 15 wherein said seat is replaceable.

17. A cannula as described in claim 13 wherein said shroud is removable from said first member.

18. A cannula as described in claim 17 wherein said shroud is attached to the first member by a threaded fastener.

19. A cannula as described in claim 18 wherein said first member bore has a replaceable seal for containing surgical instrument and said shroud is attached to said first member by a threaded cap.

20. A cannula as described in claim 18 wherein said first member has an annular flange and said shroud has an annular flat captured to the first member annular flange by a threaded cap.

21. A cannula as described in claim 13 wherein said shroud is generally conical with an open conical end for contacting said patient's skin.

22. A cannula as described in claim 13 wherein said shroud is fabricated from a polymeric material.

23. A cannula as described in claim 13 wherein said shroud is attached to said first member in a positionally adjustable manner.

24. A method for positioning a cannula, comprising:
   providing a cannula having a tissue gripping surface and a shroud disposed on one end, said cannula also having an inner bore;

inserting said cannula into a patient wherein said tissue gripping surface pulls said patient's tissue up into said shroud creating a cavity within said patient's body.

25. A method for positioning a cannula as described in claim 24 further including providing a helical treaded gripping surface and torquing said cannula to distract said patient's tissue up into said shroud.

26. A method for positioning a cannula as described in claim 24 further including removably connecting said shroud with said cannula.

27. A method for positioning a cannula as described in claim 24 further including setting the length of insertion of said cannula into said patient by selecting a shroud of a predetermined length.

28. A method for positioning a cannula as described in claim 24 further including closing the inner bore of said cannula with a seal.

29. A method for using a cannula with a receptacle member and a connected penetrating member to distract tissue away from a relatively fixed substructure, the tissue having an outer surface opposite the substructure, the method comprising:

operatively contacting the outer surface with a tissue-contacting portion of the receptacle member in a manner to define a generally bounded area of the outer tissue, and defining a void into which distracted tissue can be received with a raised portion of the receptacle;

penetrating the tissue within the generally bounded area with the penetrating member and selectably operating the penetrating member to distract the tissue into the void thereby forming a gap between the tissue and the substructure.

30. A tissue distracting cannula, comprising:

a rigid outer member configured to engage an external section of tissue;

a penetrating member attached to said outer member, said penetrating member having an internal and an external surface, said external surface having a helical thread tissue engaging surface that is capable of grasping and pulling tissue relative to said outer member that is engaging said external section of tissue.

31. A tissue distracting cannula, comprising:

an outer member configured to engage an external section of tissue;

a penetrating member attached to said outer member, said penetrating member having an internal and an external surface, said external surface having a helical thread tissue engaging surface that is capable of grasping and pulling tissue relative to said outer member that is engaging said external section of tissue and said helical thread being integrally formed on said penetrating member.

* * * * *